US006759847B2

(12) United States Patent  (10) Patent No.: US 6,759,847 B2
Brinker et al.  (45) Date of Patent: Jul. 6, 2004

(54) MAGNETIC RESONANCE IMAGING METHOD WITH ADHERENCE TO SAR LIMITS

(75) Inventors: Gerhard Brinker, Erlangen (DE); Wolfgang Renz, Erlangen (DE)

(73) Assignee: Siemens Akiengesellschaft, Munich (DE)

( * ) Notice: Subject to any disclaimer, the term of this patent is extended or adjusted under 35 U.S.C. 154(b) by 0 days.

(21) Appl. No.: 10/269,728

(22) Filed: Oct. 11, 2002

(65) Prior Publication Data

US 2003/0098688 A1 May 29, 2003

(30) Foreign Application Priority Data

Oct. 11, 2001 (DE) .......................................... 101 50 138

(51) Int. Cl.[7] .................................................. G01V 3/00
(52) U.S. Cl. ...................................... 324/309; 324/307
(58) Field of Search ................................ 324/300, 307, 324/309

(56) References Cited

U.S. PATENT DOCUMENTS

| 5,519,320 A | * | 5/1996 | Kanayama et al. | .......... 324/309 |
| 6,426,623 B1 | * | 7/2002 | Bernstein | ..................... 324/314 |
| 2003/0080738 A1 | * | 5/2003 | Brinker et al. | ............... 324/309 |
| 2003/0098687 A1 | * | 5/2003 | Arneth et al. | ................ 324/309 |

FOREIGN PATENT DOCUMENTS

| JP | 05-317287 | * | 12/1993 |
| JP | 07-222725 | * | 8/1995 |
| JP | 08-038447 | * | 2/1996 |
| JP | 11-253416 | * | 9/1999 |

OTHER PUBLICATIONS

Diana Simunic et al., "Spatial Distribution of High–Frequency Electromagnetic Energy in Human Head During MRI: Numerical Resuls and Measurements", IEEE, vol. 43, No. 1 Jan. 1996, pp. 88–94.*

Ji Chen et al., "Numerical Simulation of SAR and B1–Field Inhomogeneity of Shield RF Coils Loaded with the Human Head", IEEE, vol. 45, No. 5, May 1998, pp. 650–659.*

Patent Abstracts of Japan Publication No. 03284241 A, for Japanese Application 02087077.

* cited by examiner

*Primary Examiner*—Diego Gutierrez
*Assistant Examiner*—Dixomara Vargas
(74) *Attorney, Agent, or Firm*—Schiff & Hardin LLP

(57) ABSTRACT

In a method for magnetic resonance imaging with adherence to SAR limit values, a patient is charged with a radiofrequency pulse sequence via at least one transmission antenna for the implementation of a measurement in a magnetic resonance tomography apparatus, and the magnetic resonance signals that are produced are acquired in a spatially resolved manner via at least one reception antenna and are further-processed for producing magnetic resonance images or spectra. SAR values are determined before the implementation of the measurement on the basis of patient data and the position of the patient relative to the transmission antenna for planned parameters of the measurement, and the parameters are modified as needed until the SAR values lie within the SAR limit values. The position of the patient relative to the transmission antenna is exactly determined by an imaging magnetic resonance pre-measurement. The method enables adherence to the SAR limit values without having to take large tolerances into consideration. No additional hardware whatsoever and no positioning rule for the user are required for the realization of the method.

7 Claims, 3 Drawing Sheets

MAGNETIC RESONANCE IMAGING METHOD WITH ADHERENCE TO SAR LIMITS

BACKGROUND OF THE INVENTION

1. Field of the Invention

The present invention is directed to a method for magnetic resonance imaging with adherence to SAR (Specific Absorption Rate) limit values of the type, wherein a patient is subjected to a radio-frequency pulse sequence via at least one transmission antenna for the implementation of a measurement in a magnetic resonance tomography apparatus, and magnetic resonance signals that are produced are acquired in a spatially resolved manner via at least one reception antenna and further-processed for producing magnetic resonance images or spectra, with current SAR values being determined before the implementation of the measurement on the basis of patient data and the position of the patient relative to the transmission antenna for planned parameters of the measurement, and wherein the parameters are modified as warranted until the current SAR values lie within the SAR limit values.

2. Description of the Prior Art

Magnetic resonance tomography is a known technique for acquiring images of the inside of the body of an examination subject. For implementation of magnetic resonance tomography, a basic field magnet generates a static, relatively homogeneous basic magnetic field. Rapidly switched gradient fields for location coding that are generated by gradient coils, are superimposed on this basic magnetic field during the exposure of magnetic resonance images. Sequences of radio-frequency pulses for triggering magnetic resonance signals are emitted into the examination subject with one or more radio-frequency transmission antennas. The magnetic resonance signals produced as a result of these radio-frequency pulses are received by radio-frequency reception antennas. Tomograms of the inside of the body of the patient are calculated and displayed on the basis of the magnetic resonance signals received from the field of view (FoV) under observation, possibly covering one or more body slices of the patient.

All body regions from the head to the foot can be measured in this way by displacement of the patient bed within the magnetic resonance tomography apparatus.

The slices generated in the measurement field can be arbitrarily oriented relative to the body axes by means of an appropriate a dexterous selection of the measurement parameters, particularly parallel to the longitudinal axis in the X-Z-plane and/or the Y-Z-plane, Z indicating the direction of the longitudinal body axis that is identical to the transport direction of the patient bed, and X and Y referencing the directions orthogonal thereto. For a patient borne lying on his/her back, coronal or sagittal tomograms of the human body are thus obtained.

An important requirement in modern magnetic resonance tomography is the capability for fast imaging. This demand results from economic considerations of being able to examine as many patients as possible within a given time interval and, as well as from specific medical questions wherein a fast imaging is required for the examination result. One example of this is the reduction of motion artifacts due to movement of the patient during the measurement.

The high repetition rate of the radio-frequency transmission pulses and transmission pulse sequences required for a fast imaging, however, leads to a higher stress on the patient from electromagnetic radiation, Due to legal regulations, limit values are prescribed for this SAR (SAR=Specific Absorption Rate) stress that cannot be exceeded in magnetic resonance imaging. Since modern magnetic resonance tomography systems are technically capable of stressing patients with significantly higher SAR values, arrangements referred to as SAR monitors must be utilized in order to assure adherence to the limit values in the measurement. In addition to whole-body SAR values, specific limit values also must be adhered to for various body regions, and a fundamental distinction must be made between whole-body, partial body and local exposures.

Japanese Application 03284241 discloses a method for magnetic resonance imaging, wherein a coarse magnetic resonance image is produced before the implementation of the measurement and the region of the patient exposed in the measurement is approximately identified therewith by fitting in a circular line. An analytical calculation of the SAR values can be implemented over the radius of this circular line, this being based on the approximation of a spherical, exposed patient volume. Although the calculation can be realized with a simple equation, it leads the relatively imprecise values due to the approximation. The parameters of the planned measurement are then modified as needed until the calculated SAR values lie within the SAR limit values. The actual measurement for the magnetic resonance imaging is subsequently implemented.

The SAR stress is dependent on the individual patient data and on the position of the patient relative to the transmission antenna, the type of transmission antenna, and the transmission power, which is essentially defined by the type of pulse sequence, the flip angle of the RF pulses employed, the repetition rate and the number of simultaneously acquired slices. Antennas referred to as whole-body resonators or body resonators that are very frequently utilized in magnetic resonance tomography systems and are usually short compared to the body size of an adult patient. These resonators usually effect only a partial body exposure, so that the position of the patient relative to the transmission antenna or antennas—given the simultaneous use of a plurality of transmission antennas—is very important for the calculation of the SAR values.

Conventionally, the SAR values are calculated before the implementation of the measurement from known patient data such as age, weight and body size and from an estimated position of the patient relative to the transmission antenna for planned parameters of the measurement, and the parameters are modified as needed in order to assure adherence to the SAR values. The parameters of the measurement are thereby usually summarized in a measurement protocol. The operator must position the patient on the patient bed according to a specific user rule, so that a specific position of the patient relative to the transmission antenna can be assumed within certain limits as the basis for the calculation. For safety reasons, however, a worst-case position of the patient must be assumed in the calculation.

Due to the uncertainties in the determination of the SAR values for a patient based on the planned measurement parameters, large tolerances must be employed in the calculation which prevent an optimum utilization of the parameters allowed for the measurement.

SUMMARY OF THE INVENTION

An object of the present invention is to provide a method for magnetic resonance imaging with adherence to the SAR values that allows a better utilization of the compatibilities of the magnetic resonance tomography apparatus.

This object is achieved in accordance with the invention in a method of the type initially described wherein the position of the patient relative to the transmission antenna is exactly determined with an imaging magnetic resonance pre-measurement before the implementation of the actual measurement. On the basis of this exact position of the patient, the SAR values for planned parameters of the measurement are then calculated in a known way from known patient data and the exactly identified position of the patient relative to the transmission antenna. The parameters can be modified as warranted until the SAR values lie within the SAR limit values. Subsequently, the actual measurement for the magnetic resonance imaging of the region or regions of interest of the patient is implemented.

As a result of the exact knowledge of the position of the patient relative to the transmission antenna, the SAR stress applied locally in the measurement and averaged over the exposed regions can be very exactly determined. The measurement parameters such as, for example, the repetition rate, the number of measured slices or the type of pulse sequence utilized can be optimally utilized up to the limit values. Further, it is no longer necessary for the user to adhere to specific rules for supporting the patient on the patient bed. The present method requires no additional hardware equipment for the magnetic resonance tomography apparatus. Moreover and above this, it is not susceptible to disruption due to the use of certain accessories such as, for example, surface coils such as the CP head array or the body array coil that lie on the patient. Optical methods, in contrast, are very susceptible to disruption with respect to the aforementioned accessories.

In the implementation of the method, the position of the patient on the bed is exactly identified on the basis of the image data obtained by the imaging magnetic resonance pre-measurement after the patient has been placed onto the patient bed. The momentary position of the bed relative to the transmission antenna or antennas is exactly known in a magnetic resonance tomography apparatus. The position of the patient relative to the transmission antennas can be obtained exactly from this relationship. The measurement parameters are subsequently selected such that the SAR limit values are not exceeded. During the further course of the examination when the bed is displaced for measuring other body regions of the patient, only the new position of the bed is utilized in order to be able to indicate the modified position of the patient relative to the transmission antenna in conformity with the precision with which the bed is displaced, typically with millimeter precision. Of course, the measurement sequence for the imaging magnetic resonance pre-measurement must be selected such that the SAR limits are not exceeded by this pre-measurement. This, however, can be realized without difficulty since this pre-measurement merely involves a position determination.

The present method thus advantageously utilizes the imaging property of magnetic resonance tomography systems in order to acquire the exact patient position with the magnetic resonance system itself, i.e. by means of an image exposure with the magnetic resonance tomography system. In addition to this position, the entire body of the patient also can also be measured in advance, so that the exact geometry of the patient can also be acquired in addition to the position. This additionally improves the precision of the calculation of the SAR values. Further, the attitude of individual body regions or body parts can be identified from the acquired image data or can be calculated in advance based on the body size of the patient, so that the bed can subsequently automatically move exactly to the required measurement position given an examination of these body parts or body regions.

Various prominent body parts can be utilized as reference points of the patient body for the determination of the position of the patient relative to the transmission antenna or antennas. The allocation of the patient position relative to the bed thus can be implemented, for example, by having the user of the system mark the position of the cranium of the patient in the monitor image of the magnetic resonance pre-measurement. Further, the position of this prominent location can also be implemented in an automated manner by means of a pattern recognition method or contour recognition, so that no actions on the part of the user are required. Suitable pattern or contour recognition methods are known and are implemented with software in the image evaluation.

The imaging magnetic resonance pre-measurement can be implemented in various versions. The only requirement is that the imaging pre-measurement must enable the determination of the position of a prominent point of the patient body. This can ensue by measuring the entire body or only a body region such as, for example, the head or the feet. The acquisition of a head measurement can be easily implemented in a measurement wherein the patient is introduced into the magnetic resonance system headfirst. The same is true for the measurement of the feet in instances wherein the patient is introduced into the magnetic resonance system feet-first. Such a measurement of only a region of the body can be relatively quickly implemented in advance. Given a measurement of the entire body that, in particular, is implemented for the additional determination of the body geometry and the attitude of individual organs or body regions relative to the transmission antenna, it is advantageous not to have to provide a matching network between the radio-frequency amplifier and the transmission antenna but to instead accept mismatches. In this way, even the entire body can be measured in advance without a large time expenditure.

Of course, the present method can be implemented for arbitrary transmission antennas with which the position of the patient relative to these antennas or coils is modified by moving the patient bed.

DESCRIPTION OF THE PREFERRED EMBODIMENTS

Figure 1A:
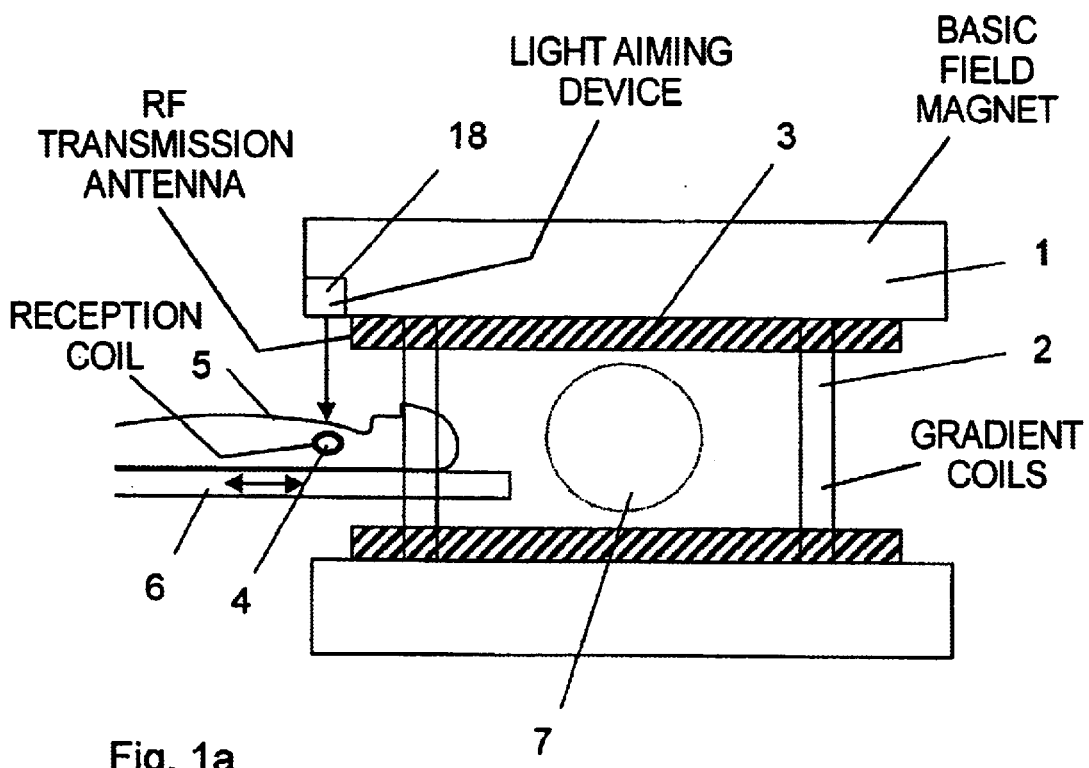
FIGS. 1a, 1b and 1c show examples of the basic components of a magnetic resonance tomography apparatus on the basis of three steps in the implementation of the present method.
Figure 1B:
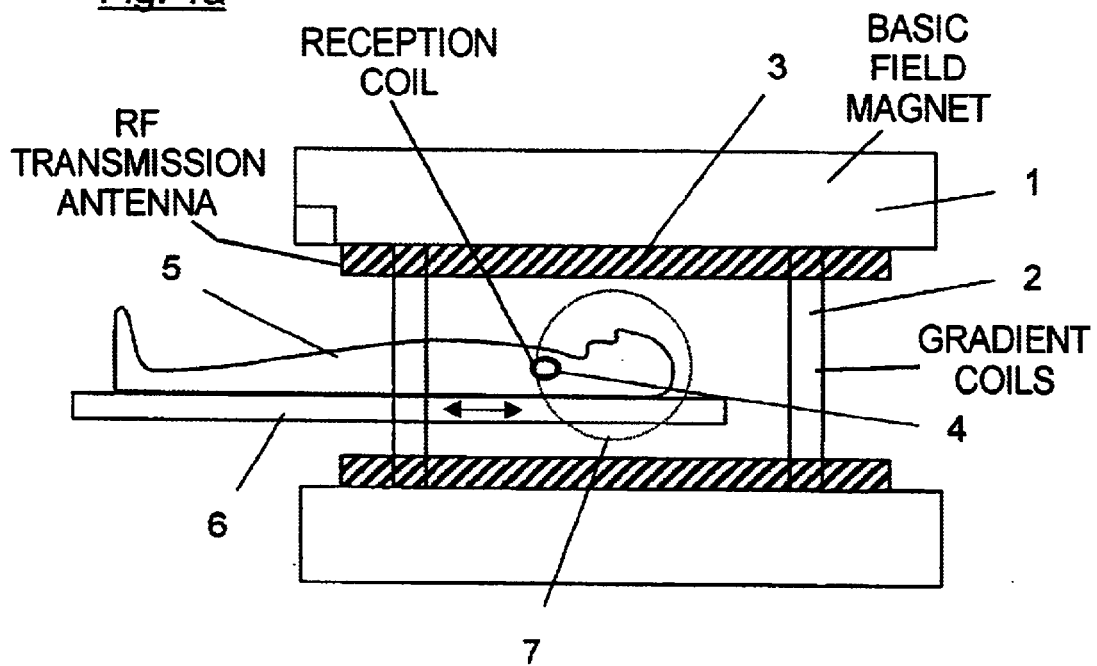
Figure 1C:
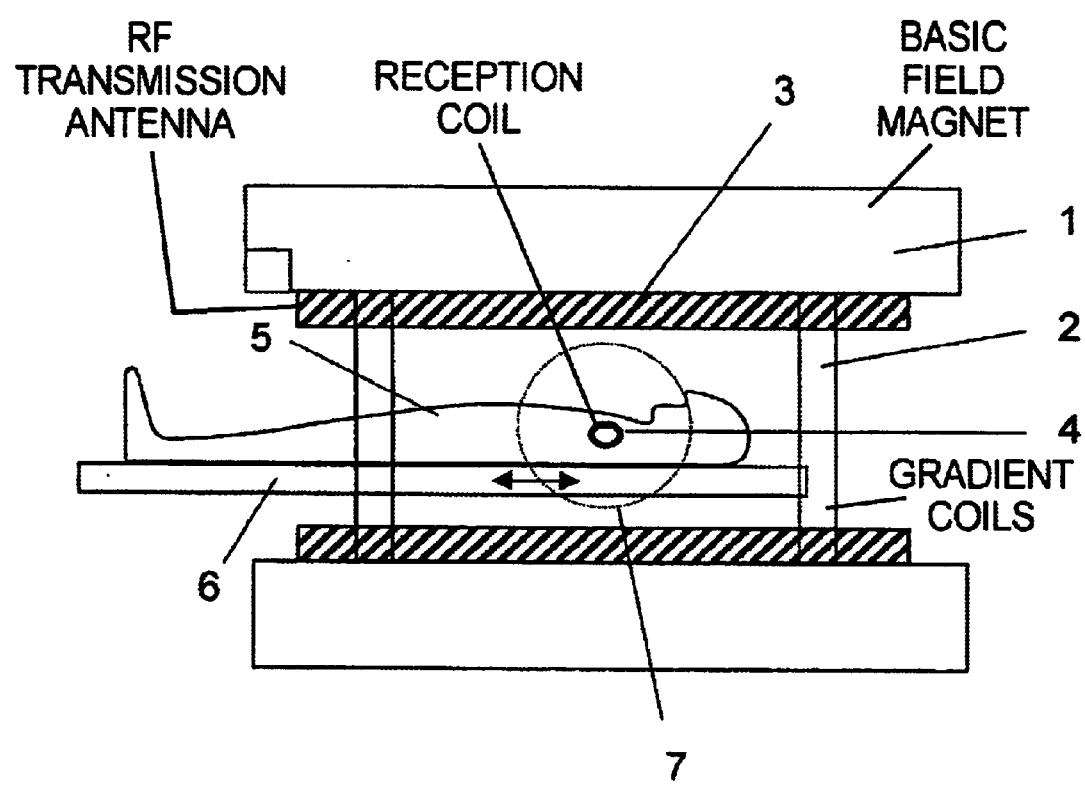

FIGS. 1a through 1c schematically show a section through a magnetic resonance tomography apparatus. FIGS. 1a–1c only show the basic components of the apparatus, a basic field magnet 1, a gradient coil system 2, a radio-frequency transmission antenna 3 as well as a reception coil 4 (Rx only). Further, a patient 5 is shown on a patient bed 6 that is movable within the magnetic resonance tomography apparatus in the direction indicated with the arrow. In the measurement, radio-frequency pulses for generating magnetic resonance signals are emitted into the body of the patient 5 via the radio-frequency transmission antenna 3 fashioned as whole-body coil. The magnetic resonance signals are acquired with the reception coil 4—in the present example—or with the radio-frequency antenna 3, which can also be operated as receiver, and are presented in the form of a two-dimensional magnetic resonance image of the measurement region 7, this being indicated broken-lines in FIGS. 1a–1c. For acquiring a number of slices, the patient is moved with the patient bed 6 by a certain distance in the indicated direction after the acquisition of the region 7 and a measurement is implemented again. In this way, either the entire body of the patient or individually designated body regions can be measured.

In conjunction with the inventive method, FIG. 1a shows a condition wherein a body region of the patient 5 to be examined, the shoulder in the present example, is marked with a light-aiming device 18. The local reception coil 4 for the later measurement is placed on the shoulder. Subsequently, the patient is moved farther into the tomography apparatus with the patient bed 6 up to a position in which it is expected the head position lies within the measurement field (FoV) 7. The imaging magnetic resonance pre-measurement is implemented in this position (FIG. 1b). The whole-body resonator is preferably utilized in this pre-measurement for the acquisition of the magnetic resonance signals. Pure reception coils such as, for example, a head coil also can be utilized in this pre-measurement for improving the image quality. Finally, the head position is identified from the magnetic resonance pre-measurement. As a result of the identification of the head position and obtaining the data acquired in the patient registration, the body region previously marked with the light-aiming device 18 can now be automatically determined for the calculation of the SAR values. This body region is then approached for the planned measurement so that it lies in the center of the measurement field 8 (FIG. 1c).

Figure 2:
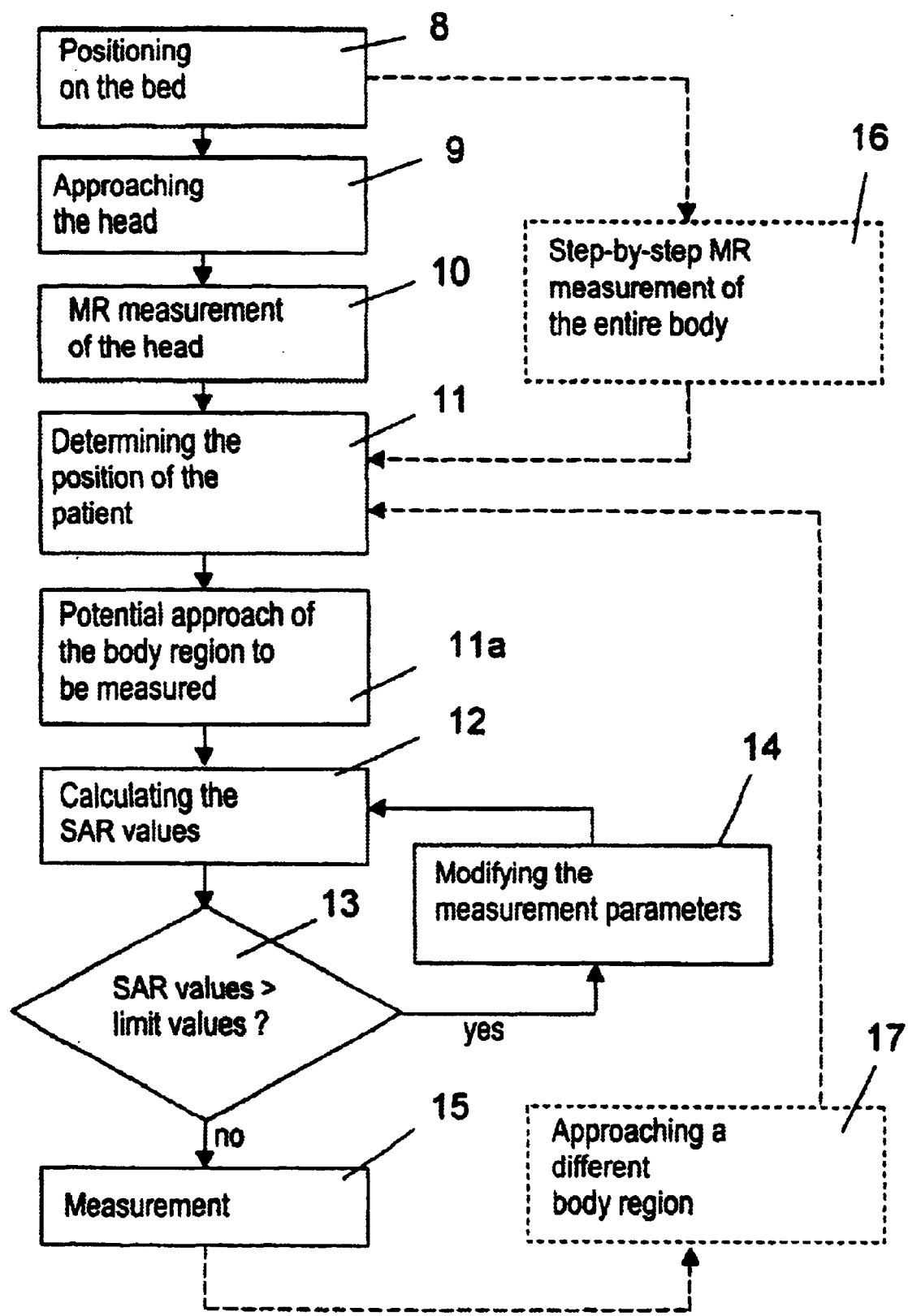
FIG. 2 is a flowchart of an example for the implementation of the present method.

FIG. 2 shows a flowchart for the implementation of an exemplary embodiment of the present method. The patient is initially placed on the patient bed 6, moved out of the examination region, so that the patient can be introduced headfirst into the examination region (step 8). The user of the system first marks the body region of interest or the region to be measured with the light-aiming device 18 (FIG. 1a). Subsequently, the patient bed 6 is automatically moved into the magnetic resonance tomography apparatus so that the patient's head lies approximately in the region of the measurement field (step 9; also see FIG. 1b). After this position has been reached, an imaging magnetic resonance pre-measurement is implemented with a measurement field (FoV) that has been selected adequately large (step 10). The acquired image is subjected to a pattern recognition wherein the head or the cranium is recognized and placed into relationship with the position of the transmission antenna via the known bed position. Using the physical data of the patient acquired in the patient registration, the exact position of the patient on the bed 6 and—given arbitrary bed positions—relative to the transmission antenna 3 as well is thus known (step 11). Subsequently, the patient is moved into the initially marked position with the bed (step 11a; also see FIG. 1c). The SAR calculation for the desired position is not implemented (step 12). The parameters are thereby selected such that the limit values are not exceeded. In the present case, the SAR limit values relate to the measurement of the patient's head. When the planned parameters of the measurement sequence lead to elevated SAR values, then the repetition rate and/or the number of slice to be measured is reduced until the limit values are reached or, respectively, downwardly transgressed (step 13 and 14). Further, of course, the flip angle or other suitable parameters also can be modified for this purpose. In an alternative, a different measurement sequence having a similar image result also can be selected when this leads to lower SAR values. The actual measurement or examination is subsequently implemented (step 15).

An alternative of the present method as shown on the basis of the broken-line flow in the flowchart in the upper area of FIG. 2, in which the patient is positioned on the patient bed 6 in the same way as in the embodiment explained above and the region of interest is marked with the light-aiming device 18 (step 8). Subsequently, the bed 6 is displaced relative to the transmission antenna 3 in steps that correspond to the measurement field or FoV 7 that has been set. At every step, a coronary and/or sagittal image of a slice of the patient body is registered in the framework of the imaging magnetic resonance pre-measurement (step 16). The exact position of the patient relative to the bed 6 or transmission antenna 3 is determined from the acquired image data via a pattern recognition (step 11). Subsequently, the determination of the measurement parameters with adherence to the SAR limit values is implemented in the same way as explained in the preceding embodiment (steps 12 through 14). The position of the patient relative to the transmission antenna 3 is thereby exactly known dependent on the current bed position. In addition to this information, the image data contain the geometrical dimensions of the patient, so that these are likewise utilized for the calculation of the SAR values. Identification of the dimensions and the weight of the patient in the framework of the patient registration are no longer required since these are known from the measured data or can be derived, in the case of weight.

Optionally, an arbitrary body region of the patient can be exactly approached with the bed 6 in this exemplary embodiment (step 17), as indicated by the broken-line course in the lower part of the Figure, since the exact position of every body region on the bed and, thus, the position relative to the transmission antenna is known as a result of the pre-measurement (step 11). Given prescription of one or more corresponding body regions, the bed 6 thus can automatically approach the measurement position for measuring these regions with high precision.

Although modifications and changes may be suggested by those skilled in the art, it is the intention of the inventors to embody within the patent warranted hereon all changes and modifications as reasonably and properly come within the scope of their contribution to the art.

We claim:
1. A method for magnetic resonance imaging with adherence to Specific Absorption Rate (SAR) limit values, comprising the steps of:
conducting a magnetic resonance examination having planned parameters associated therewith, of a patient having patient data associated therewith, by exposing said patient to a radio-frequency pulse sequence using at least one radio-frequency transmission antenna to produce magnetic resonance signals in said patient, acquiring said magnetic resonance signals from said patient in a spatially resolved manner via at least one reception antenna, and processing said magnetic resonance signals to obtain an examination result selected from the group consisting of a magnetic resonance image and a spectrum;
before conducting said magnetic resonance measurement, identifying a position of said patient relative to said transmission antenna by an imaging magnetic resonance pre-measurement; and before conducting said magnetic resonance measurement, determining SAR values dependent on said patient data and said position of the patient relative to the transmission antenna, and modifying said planned parameters as needed until said SAR value is within a predetermined SAR limit.

2. A method as claimed in claim 1 comprising obtaining a magnetic resonance image of an entirety of said patient in said imaging magnetic resonance pre-measurement.

3. A method as claimed in claim 1 comprising obtaining an image only of a region of a body of said patient in said imaging magnetic resonance pre-measurement.

4. A method as claimed in claim 1 comprising selecting at least one parameter from the group consisting of a repetition rate of said radio-frequency pulse sequence, a plurality of slices of said patient from which said magnetic resonance signals are obtained, a thickness of a slice of said patient from which said magnetic resonance signals are obtained, and a flip angle of pulses in said radio-frequency pulse sequence, as a parameter which is varied until said SAR value is within said SAR limit.

5. A method as claimed in claim 1 wherein said patient has a prominent body part, and comprising including said prominent body part in said imaging magnetic resonance pre-measurement, and using said prominent body part to identify said position of said patient relative to said transmission antenna.

6. A method as claimed in claim 1 comprising the additional steps of determining an attitude of a body region of said patient, from which said magnetic resonance signals are to be obtained in said magnetic resonance examination, from said imaging magnetic resonance pre-measurement, and approaching said body region in automated fashion during said magnetic resonance examination dependent on said determination.

7. A method as claimed in claim 1 comprising the additional steps of pre-calculating an attitude of a body region of said patient, from which said magnetic resonance signals are to be obtained in said magnetic resonance examination, from said imaging magnetic resonance pre-measurement, and approaching said body region in automated fashion during said magnetic resonance examination dependent on said pre-calculation.

* * * * *